United States Patent [19]

Goupil

[11] Patent Number: 5,360,816
[45] Date of Patent: Nov. 1, 1994

[54] 5-METHOXY PSORALEN USED TO TREAT PSORIASIS

[76] Inventor: Jean-Jacques Goupil, 30 Avenue du Président Wilson, 94230 Cachan, France

[21] Appl. No.: 879,539

[22] Filed: May 4, 1992

Related U.S. Application Data

[60] Continuation of Ser. No. 749,491, Aug. 15, 1991, abandoned, which is a continuation of Ser. No. 352,705, May 10, 1989, abandoned, which is a continuation of Ser. No. 201,384, May 31, 1988, abandoned, which is a continuation of Ser. No. 825,783, Feb. 3, 1986, abandoned, which is a continuation of Ser. No. 724,496, Apr. 18, 1985, abandoned, which is a continuation of Ser. No. 547,947, Nov. 2, 1983, abandoned, which is a division of Ser. No. 195,414, Oct. 9, 1980, abandoned, which is a continuation of Ser. No. 953,118, Oct. 20, 1978, abandoned.

[51] Int. Cl.$^5$ .............................. A61K 31/35
[52] U.S. Cl. .................................... 514/455
[58] Field of Search .......................... 514/455

[56] References Cited

U.S. PATENT DOCUMENTS

| | | | |
|---|---|---|---|
| 4,130,568 | 12/1978 | Confolone et al. | 260/343.21 |
| 4,147,703 | 4/1979 | Liebman et al. | 260/343.21 |
| 4,217,445 | 8/1980 | Nikolaiski | 536/4 |

OTHER PUBLICATIONS

Chemical Abstracts 64:4125f (1966).
Handbook of Nonprescription Drugs, 5th ed., 1977, pp. 331–333.

Primary Examiner—Marianne M. Cintins
Assistant Examiner—T. J. Criares
Attorney, Agent, or Firm—Darby & Darby

[57] ABSTRACT

A pharmaceutical formulation comprising 5-methoxy psoralen, which is useful in the treatment of psoriasis and other skin disorders, is disclosed herein. 5-methoxy psoralen may be synthesized from phloroglucinol by a five step process which is also disclosed.

8 Claims, No Drawings

5-METHOXY PSORALEN USED TO TREAT PSORIASIS

"This is a continuation of application Ser. No. 07/749,491, filed Aug. 15, 1991, now abandoned which in turn is a continuation of Ser. No. 07/352,705 filed May 10, 1989, now abandoned which is a continuation of Ser. No. 07/201,384 filed May 31, 1988, now abandoned which is a continuation of Ser. No. 06/825,783, filed Feb. 3, 1986, now abandoned which is a continuation of Ser. No. 06/724,496 filed Apr. 18, 1985, now abandoned which is a continuation of Ser. No. 547,974 filed Nov. 2, 1983, now abandoned which is a Div. of Ser. No. 06/195,414 filed Oct. 9, 1980, now abandoned which is a continuation of Ser. No. 05/953,118 filed Oct. 20, 1978, now abandoned.

BACKGROUND OF THE INVENTION

This invention relates to a new medicament characterized by the fact that it contains, as the active substance, 5-methoxy psoralen having the formula

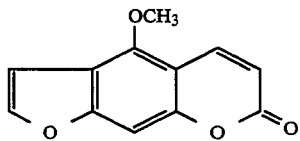

It is known that certain furocoumarins, including psoralen and certain of its derivatives, exhibit a photodynamic activity which gives rise to photodermatitis. This dermatitis appears after oral or topical administration of the furocoumarins to a mammal and exposure to the sun or to ultra-violet rays.

In the studies which have been carried out on the phototoxicity of psoralen and its derivatives, it has been shown that the most photodynamic or phototoxic composition was psoralen itself having the formula

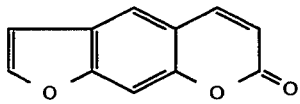

followed, in decreasing order, by 4'-methyl-psoralen, 8-methoxy-psoralen 4,5'-dimethylxanthotoxin, 4-methylxanthotoxin, 5-methoxy-psoralen, and 5-ethoxy-psoralen. The decrease in the phototoxicity within this group is substantial. The phototoxicity of 8-methoxy-psoralen, is only 37.5% of that of psoralen; the phototoxicity of 5-methoxy-psoralen is only 27.5% of that of psoralen.

It has been found that the therapeutic activity of the psoralens is directly proportional to their phototoxicity. It has also been found that 8-methoxy-psoralen is useful in the treatment of psoriasis. This treatment is known and is generally carried out in the following fashion: 8-methoxy-psoralen is administered orally followed several hours later by irradiation with ultraviolet A rays of large wavelength (360 nanometers) and high intensity. This treatment is carried out twice a week and the maximum dose of 8-methoxy-psoralen administered is on the order of 50 mmg. The results obtained are good in that an extensive "bleaching" of the psoriasis is obtained. The secondary effects observed are the appearance of erythemas, nausea, pruritis, and headache, which result from the toxicity of the product and the intense irradiation.

In accordance with the present invention it has been discovered that, contrary to what might have been believed, another derivative of psoralen which is less phototoxic than 8-methoxy-psoralen and, therefore, less therapeutically active, displays a number of completely unexpected properties which make it much more suitable for therapeutic use and in particular more effective in the treatment of psoriasis.

This derivative is 5-methoxy-psoralen. It can be extracted from natural or synthetic bergamot oil by the method of preparation disclosed below.

The phototoxicity of 5-methoxy-psoralen is less than that of 8-methoxy-psoralen by about 20-30%. This has been confirmed by comparative clinical studies which have been carried out and involved the oral administration of 40 mmg doses of the two compounds.

5-methoxy-psoralen has also been found much less phototoxic than 8-methoxy-psoralen when administered locally at a concentration of more than 100 ppm.

The present invention also relates to a new synthesis of 5-methoxy-psoralen of the formula:

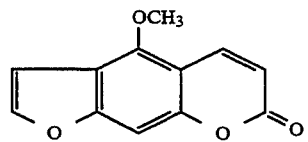

starting from phloroglucinol of the formula:

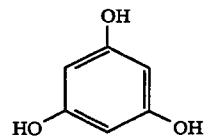

In this synthesis the phloroglucinol is methylated to obtain phloroglucinol mono-methyl ether, which is in turn cyclicized to obtain 6-hydroxy-4-methoxy-3-coumaranone; the coumaranone is reduced in one step to obtain 6-hydroxy-4-methoxy coumaran; the coumaran is then cyclicized to obtain 3,4,4',5'-tetrahydro-5 methoxy psoralen; and that product is hydrogenated to yield 5-methoxy-psoralen.

Other syntheses for psoralen derivatives are also known. For example, TETRAHEDRON LETTERS No. 59 1969, Pergamon Press, Great Britain, pp. 5223-24 discloses syntheses of xanthotoxol and xanthotoxin, having the formulas:

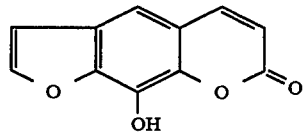

and

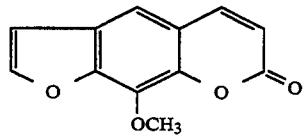

, respectively. Of these, xanthotoxin has skin photosensitizing activity, whereas xanthotoxol is practically inactive. Neither of these compounds are recognized as being useful therapeutic agents.

The method of synthesizing 5-methoxy-psoralen in accordance with the present invention is of particular interest since the starting material is inexpensive, the synthesis is carried out in fewer steps than the known syntheses of other psoralen derivatives, an inexpensive catalyst may be used for the reduction of the coumaranone which is free of the drawbacks of aging and regeneration inherent in other catalysts, and it gives good yields. It is an object of the present invention to provide a new pharmaceutical formulation comprising 5-methoxy-psoralen.

A further object of the present invention is to provide a method of treating psoriasis and other skin conditions by administration of pharmaceutical formulations which contain 5-methoxy-psoralen.

A still further object of the present invention is to provide a new process of synthesizing 5-methoxy-psoralen.

These and other objects of the present invention will be understood in conjunction with the following detailed specification.

DETAILED DESCRIPTION OF THE INVENTION

The use of 5-methoxy-psoralen as a therapeutic agent has been found to be extremely beneficial in view of its low toxicity. A comparative study of the acute toxicity of 5-methoxy-psoralen and 8-methoxy-psoralen was carried out on male mice and rats free of specific pathogens. All of the test animals were given nothing but water for 18 hours prior to the tests.

All of the animals were kept under observation for 14 days after the single oral administration in order to detect any delayed toxicity. The $LD_{50}$ and its confidence limits were calculated by the graphical method of J.T. Litchfield and F. Wilcoxon.

In these tests administration of the drug was effected orally, the dispersing agent being a 2% aqueous solution of carboxymethylcellulose to which 0.55 of Tween-80 (surfactant) had been added. In the male mice there was found an $LD_{50}$ in 14 days of 875 mmg/kg for 8-methoxy-psoralen and of 8100 mmg/kg for 5-methoxy-psoralen. In male rats the $LD_{50}$ in 14 days was 4400 mmg/kg for 8-methoxy-psoralen and higher than 30,000 mmg/kg for 5-methoxy-psoralen.

In conclusion, it may be assumed that the 5-methoxy-psoralen administered orally is about 9.25 times less toxic than 8-methoxy-psoralen.

Similar experiments were carried out on guinea pigs and showed that in the case of this animal 5-methoxy-psoralen is only about 1/17 as toxic as 8-methoxy-psoralen.

This large decrease in acute toxicity in the case of 5-methoxy-psoralen,. together with a relatively slight decrease in the therapeutic activity was completely unexpected in view of the prior art.

Because of this property of decreased toxicity, 5-methoxy-psoralen can be used in therapeutic doses which are far higher than the maxima which can be used in the case of 8-methoxy-psoralen, while nonetheless remaining at very low levels of toxicity.

If one defines the therapeutic index as the ratio between therapeutic activity (measured by phototoxicity) and acute toxicity, and assumes that in the case of 8-methoxy-psoralen this ratio is 100 to 100, i.e. 1, then for 5-methoxy-psoralen it will be 75 (25% decrease in the therapeutic activity) to 6 (toxicity one seventeenth as much), that is to say 12.5.

It can therefore be concluded that the therapeutic index of 5-methoxy-psoralen is 8 to 12 times greater than that of 8 -methoxy-psoralen.

Under these conditions, one can use therapeutic doses of 5-methoxy-psoralen which are up to five times greater than those used in the case of 8-methoxy-psoralen. This is a considerable increase in dosage.

The long-term general toxicity of 5-methoxy-psoralen was also studied in treatments of rabbits by gastric administration and application of the drug to the skin. The results were as follows:

In the case of the gastric administration of 5-methoxy-psoralen for 42 consecutive days in a dose of 300 mmg/kg/day, the toxicological study (general condition, examination of the skin and of the eye ground, hematological examination, clinical chemical examination, and anatomopathological examination) shows that the drug is very well tolerated and does not supply any element which might limit its controlled clinical use on humans.

The toxicological conclusions are the same in the case of application to the skin for 42 consecutive days by the painting on of an oily solution of a constant concentration of 30 ppm of the new drug twice a day. The only irritating effects on the skin which could be noted corresponded to the expected normal action.

The pharmacological activity of 5-methoxy-psoralen was studied in patients suffering from psoriasis and it was found that this product, administered orally or locally and activated by irradiation with A ultraviolet rays caused the disappearance of psoriasis plaques and led to a remarkable "bleaching".

For oral administration, the dosage range is from 40 mmg to 300 mmg of 5-methoxy-psoralen per treatment session and between 60 and 150 mmg. Treatment is generally administered at least once a week . The dose selected in each instance will of course always be a function of the specific sensitivity of the patient being treated. The number of treatments required to alleviate each patient's condition will vary depending on the severity of condition and the individual characteristics of each patient being treated.

The new medicament may be supplied in different forms, such as tablets, capsules, ointments, powders, creams and solutions etc. When supplied as tablets, suitable vehicles are employed, having a base, for instance, of lactose and Encompress. The tablets may be formulated using conventional procedure employing solid carriers and lubricants well known in the art. Examples of solid carriers include starch, sugar, bentonite and other commonly used carriers.

The following example of a tablet containing 20 mmg of 5-methoxy-psoralen is given by way of illustration and not of limitation.

Composition of a tablet of a total weight of 0.350 g:

| | |
|---|---|
| 5-methoxy-psoralen | 0.020 g |
| Encompress | 0.159 g |
| Lactose | 0.159 g |
| Explotab | 0.0104 g |
| Magnesium stearate | 0.0016 g |

The tablets may, of course, contain more than 20 mmg of 5-methoxy-psoralen, up to 100 mmg. The quantity of effective dose supplied by each capsule or tablet is relatively unimportant since the total dosage can be reached by administration of either one or a pluralilty of capsules or tablets or both.

The capsules employed may comprise any well known pharmaceutically acceptable material, such as gelatin, cellulose derivatives etc.

From the numerous clinical experiments carried out the following cases have been selected.

Case No. 1

A male patient suffering from psoriasis on 50% of the surface of his body was treated with the new drug in the form of tablets containing 20 mmg.

He received three tablets via the oral route, namely 60 mmg of 5-methoxy-psoralen, about 2 hours before the irradiation with A ultraviolet rays. At the start of the treatment, an energy of 3 joules/cm$^2$ was used, reaching 10 joules/cm$^2$ at the end of the treatment.

Treatment session were held four times a week.

At the end of 30 sessions a 95% "bleaching" was obtained, that is to say disappearance of the psoriatic spots.

Tolerance to the drug was excellent. The patient suffered no nausea or headache.

Case No. 2

A female patient suffering from psoriasis was treated with the new drug in the form of tablets containing 40 mmg of active compound.

She took two tablets, namely 80 mmg of 5-methoxy-psoralen, two hours before the irradiation with A ultraviolet rays. The irradiation was increased gradually from 4 joules/cm$^2$ to 10 joules/cm$^2$ at the end of the treatment. The treatment sessions were held four times a week.

At the end of 26 sessions a 95% "bleaching" of the psoriasis plagues was obtained with complete tolerance to the drug. The patient did not experience any nausea or erythema.

Case No. 3

A male patient suffering from psoriasis took two tablets of 20 mmg, namely 40 mmg of 4-methoxy-psoralen, two hours before an irradiation session with A ultraviolet rays. The irradiation was increased gradually from 1.5 joules/cm$^2$ to 9 joules/cm$^2$ at the end of the treatment. The sessions were held four times a week.

A positive result of more than 95% "bleaching" of the psoriasis plaques was obtained by the end of 19 sessions, and there was no recurrence within five months. The drug was well tolerated by the patient without any noticeable side effects.

Case No. 4

A female patient suffering from psoriasis received 5 tablets of 20 mmg each, namely 100 mmg of 5-methoxy-psoralen two hours before an irradiation session with A ultraviolet rays. The irradiation was increased gradually from 1 to 8 joules/cm$^2$ at the end of the treatment. The sessions were held four times a week.

A bleaching of more then 95% was obtained at the end of the 12th week. The patient's tolerance of the drug was excellent.

The administration of 5-methoxy-psoralen locally (topically) in the treatment of psoriasis can be effected in different forms, such as oily solutions, aqueous emulsions and ointments.

In general, the concentration of 5-methoxy-psoralen in these forms for local administration is between 100 ppm and 1000 ppm. The irradiation with A ultraviolet rays is effected about 2 hours later.

There are given below, by way of illustration, a few examples of suitable vehicles, that is to say vehicles which assure good solubility of the active product, good penetration of the skin, and good stability of the preparation.

EXAMPLE OF AN OIL VEHICLE

| | |
|---|---|
| Wheatgerm oil | 1.0 g |
| Isopropyl Myristate | 24.9 g |
| Butyl-hydroxy-toluene | 0.1 g |
| Peanut oil q.s.p. | 100.0 g |

EXAMPLE OF AN AQUEOUS EMULSION

| | |
|---|---|
| 1,2-propylene glycol | 70 g |
| Benzalkonium | 2 g |
| Cetyl alcohol (Cetiol V) | 24 g |
| Lanette wax O | 16 g |
| Spermaceti | 8 g |
| Distilled water q.s.p. | 1000 g |

EXAMPLE OF A VEHICLE FOR AN OINTMENT

| | |
|---|---|
| Sodium Lauryl sulfate | 1.00 g |
| Propylene glycol | 6.00 g |
| Stearylic alcohol | 10.00 g |
| Vaseline | 46.00 g |
| Methyl parahydroxybenzoate | 0.05 g |
| Purified water q.s.p. | 100.00 g |

In the above indicated concentrations of 100 to 1000 ppm, 5-methoxy-psoralen applied locally gives good results in the treatment of psoriasis, but with a speed of action which is slower at times than that obtained in oral treatments.

Local treatment is particularly recommended in the case of localized psoriasis, particularly at the joints. The local treatment has a remarkable effect on stubborn patches which may remain after oral treatment.

Starting with a concentration of 300 ppm, there is 100% bleaching, with total disappearance of the stubborn patches.

The efficiency is the same whatever the galenic preparation selected. Patients seem to prefer to receive the drug in the form of the oil vehicle. The tolerance level is very good, aside from a few benign erythemas of no significance.

By way of illustration, the following experiments may be cited.

Case No. 1

A male patient suffering from psoriasis and treated with 5-methoxy-psoralen orally in an amount of 50 mmg per session and A ultraviolet irradiation of an energy ranging from 1.5 joules/cm$^2$ to 5.5 joules/cm$^2$ showed, at the end of the 25th session, an 85% improvement, but several psoriatic patches persisted.

He was then treated by local applications to the persistent patches of an oil solution containing 200 ppm of 5-methoxy-psoralen before each irradiation session. A total disappearance of the stubborn psoriatic patches was noted by the end of ten sessions. 100% psoriatic bleaching was effected with perfect tolerance of the drug by the patient.

Case No. 2

A male patient whose situation was similar to that of the preceding case, that is to say showing stubborn patches after 29 irradiation sessions upon oral administration of 40 mg of 5-methoxy-psoralen and an improvement of 90%, was treated with local applications of emulsions containing 300 ppm of 5-methoxy-psoralen before the irradiation session with A ultraviolet rays of an energy of 7 joules/cm² 100% bleaching was noted by the end of the 7th session.

The drug was well tolerated by the patient and there is no recurrence of psoriasis after 6 months.

Case No. 3

A child suffering from psoriasis started treatment with 40 mmg/session of 5-methoxy-psoralen in tablet form via the oral route. Starting with the tenth session a local application of an emulsion containing 400 ppm of 5-methoxy-psoralen was added. The A ultraviolet irradiation had an energy ranging from 2 to 8 joules/cm². Bleaching was obtained at the end of the tenth session of combined oral and topical treatment. The patients tolerance of the drug was excellent.

One can also use 5-methoxy-psoralen in the form of baths in concentrations on the order of 1500 mm9 to 150 liters of hot water. The bath usually lasts about 21 minutes and is immediately followed by the A ultraviolet irradiation session. These sessions, at the rate of two a week, give excellent results.

It is to be noted with regard to the intensity of irradiation that the low toxicity of 5-methoxy-psoralen and the correlative increased amount of the doses which can be used makes it possible to reduce the useful energy of the A ultraviolet rays. This has the effect of decreasing the possible long-term toxic effects to the patient of repeated irradiations.

It should be pointed out that 5-methoxy-psoralen has been found to be useful and effective in the treatment of various dermatoses, vitiligo, atypical eczema and fungoid mycosis.

In accordance with the present invention, 5-methoxy-psoralen of the formula:

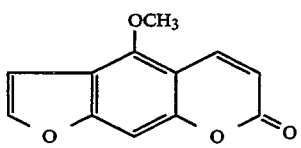

is synthesized from phloroglucinol of the formula:

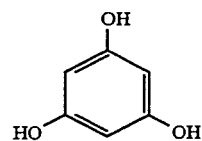

Phloroglucinol is selected as the starting material due to the presence of three hydroxy groups on its ring.

In a first step, methylation is effected with methanol in the presence of a stream of gaseous hydrogen chloride and a mixture of mono- and di-methyl ethers of phloroglucinol is obtained. The monomethyl ether of the formula:

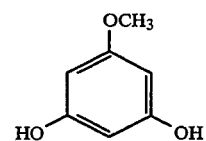

is extracted from the mixture of mono- and di-methyl phloroglucinol ethers by fractional distillation.

In this way, the methoxy substituent of 5-methoxy-psoralen is inserted in the desired position in the first step.

In a second step, the phloroglucinol monomethyl ether is cyclicized in order to obtain 6-hydroxy-4-methoxy-3-coumaranone of the formula:

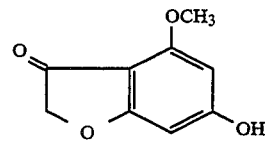

A first reaction with chloroacetonitrile, gaseous hydrogen chloride, and zinc chloride leads to a mixture of the desired coumaranone and 4-chloraceto-5-methoxy resorcinol of the formula:

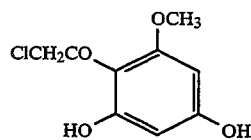

The resorcinol is in turn cyclicized to form the desired coumaranone by subjecting the coumaranone/resorcinol mixture to heating with potassium acetate under reflux.

In a third step the 6-hydroxy-4-methoxy-3-coumaranone is converted into 6-hydroxy-4-methoxy-coumaran by direct reduction, using hydrazine hydrate as a catalyst.

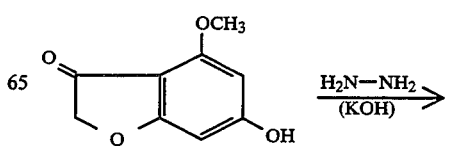

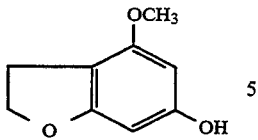

This direct reduction of the 6-hydroxy-4-methoxy-3coumaranone is entirely new. The methods of reduction employed in the prior art comprise several steps. In particular, the reduction with a palladium-carbon catalyst requires the prior protection of the hydroxyl group by an acetylation with acetyl chloride and then, after reduction, a deacetylation in order to liberate the hydroxyl group and continue with the cyclization reactions.

In accordance with the present invention, the direct reduction into coumaran is effected by dissolving the 3-coumaranone in diethylene glycol using heat, adding 98% hydrazine hydrate, heating under reflux for 15 minutes with the formation of the corresponding hydrazone, adding caustic potash in the form of pellets after the solution has been cooled and bringing the solution to a mild boil for 10 hours. After acidification to a pH of 7.5, extraction under heat with ether in liquid-liquid countercurrent, distillation, and recrystallation, fine light-yellow crystals of coumaran were obtained in a yield of 70%.

This reaction of direct reduction of the hydroxy methoxy coumaranone is possible due to the selection of hydrazine hydrate as reduction catalyst. The latter acts selectively and does not react with the hydroxylated group. The advantages of this process are numerous: elimination of at least two steps, acetylation and deacetylation, selection of a catalyst of good reduction capacity which is less expensive than palladium catalysts, and absence of problems that are attributable to aging and regeneration of the catalyst.

In a fourth step the 6-hydroxy-4-methoxy-coumaran is cyclicized to form 3,4,4',5'-tetrahydro-5-methoxy-psoralen with acrylonitrile, zinc chloride and a stream of gaseous hydrogen chloride.

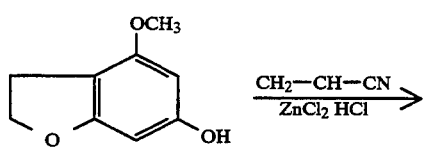

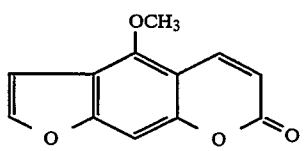

In a fifth step, it is necessary to dehydrogenate the preceding compound, either with palladium-treated carbon, chloranil, or any other dehydrogenating agent in order to obtain 5-hydroxy-psoralen of the formula This product, which is obtained in the form of thin colorless pearly flakes of MP=188° C., has IR, UV and NMR spectra which are identical to those of the natural product.

In detail, the method of operation of this new snythesis is as follows:

EXAMPLE 1

1st step: Preparation of phloroglucinol monomethyl ether. Reaction:

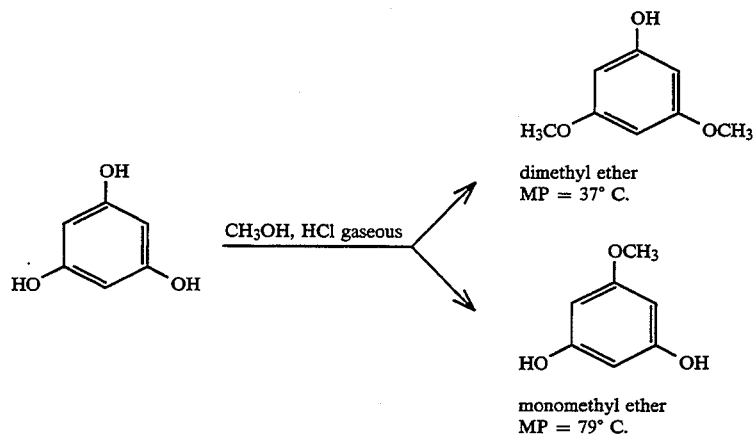

In a round-bottom flask provided with a reflux condenser and a dip tube extending to the bottom of the reaction mixture, introduce:
—40 g of anhydrous phloroglucinol
—200 ml of methanol (absolute).

While passing a slow stream of gaseous HCl through it, reflux the mixture for three hours to maintain saturation (about 15 g of gaseous HCl are absorbed). The refluxed mixture is set aside overnight.

The excess methanol is expelled on a water bath under slight vacuum (this recovered alcohol can serve for a new methylation).

The syrupy residue is taken up in 50 ml of water and 50 ml of ether. The mixture is decanted and extracted two more times, using 50 ml of ether each time.

The ether solutions are combined, washed with water and then with a solution of 5% NaHCO₃, until neutral, and finally washed with water again and dried over anhydrous calcium chloride. The solution is filtered and the excess ether expelled on a water bath.

The residue left after the expulsion is fractionated under reduced pressure:

a) the di-methyl ether is contained in the head fractions $BP_{15} 180°-195°$ C.;

b) there is a mixture of the di-methyl and monomethyl ethers in the middle fractions: $BP_{15} 195°-210°$ C.

The middle fractions are triturated cold in toluene to dissolve the diether.

The solution is then suction filtered and washed with toluene; colorless crystals of monomethyl ether are obtained of $C_7H_8O_3$ Molecular weight: 140

Yield: 55%.

Analysis gave the following results:

|  | calculated | found |
|---|---|---|
| Carbon % | 60.5 | 59.98 |
| Hydrogen % | 05.76 | 05.80 |
| Oxygen % | 34.29 | 34.30 |

2nd step: Preparation of 6-hydroxy-4-methoxy-3coumaranone.

Reaction:

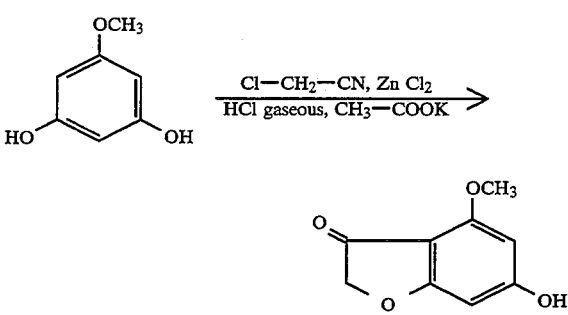

A stream of gaseous HCl is bubled through a well-cooled (and vigorously agitated)-suspension of:

—40 ml of anhydrous ether or ligroin (BP=40°-60° C.)

—7.70 g (or 0,055 tool) of phloroglucinol monomethyl ether

—4 g (or 0.053 mol) of freshly fractionated chloracetonitrile

—4 g (or 0,003 mol) of zinc chloride (melted and pulverized) for 35 minutes.

The ketimine hydrochloride is suction filtered, and washed twice with 10 ml of anydrous ether. It is dissolved in 200 ml of distilled water (the final traces of ether accompanying the aqueous solution are eliminated by suction filtration with a water pump).

This aqueous solution is heated under reflux for 10 minutes and then set aside overnight in a refrigerator.

A precipitate is formed which is a mixture of two products, namely:

1) 6-hydroxy-4-methoxy-3-coumaranone and 2) 4-chloracetyl-5-methoxy-1,3-resorcinol (of yellow color)

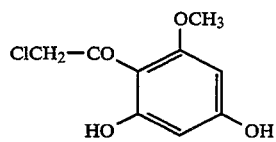

This mixture is dried and washed twice with 20 ml of ice water per wash. Dry. Weight: about 8.30 g.

The mixture is then treated to cyclizate the 4-chloracetyl-5-methoxy-1,3-resorcinol by introducing it into a solution of 5 g of potassium acetate in 25 ml of absolute ethanol.

The reaction mixture is heated under reflux for 15 minutes, chilled, and poured into 69 ml of ice water.

The precipitate is vacuum filtered and recrystallized it from about 30 ml of boiling water.

Upon cooling, the coumaranone sought is present in the form of fine light-yellow needles MP: 305° C.

Yield: about 80%.

$C_9H_8O_4$ Molecular weight: 180

Results of elementary analysis are as follows:

|  | calculated | found |
|---|---|---|
| Carbon % | 60.5 | 59.98 |
| Hydrogen % | 4.48 | 4.59 |
| Oxygen % | 35.56 | 35.50 |

TLC: Silicagel F-1500 LS-254

Solvent: Methylene chloride/ethanol: 30/5 $R_f$ about 0.76.

Ferric chloride test: positive (for-the OH grouping).

3rd step: Preparation of 6-hydroxy-4-methoxy-coumaran

Reaction:

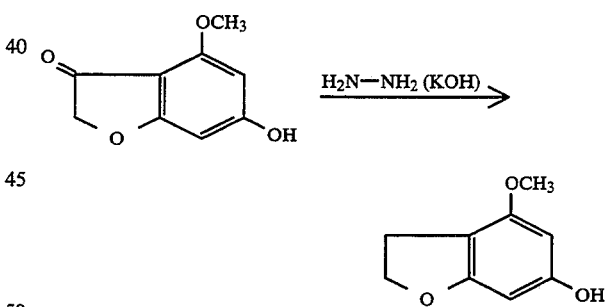

10 g of 6-hydroxy-4-methoxy-3-coumarannon is dissolved in 100 ml of diethylene glycol, using heat.

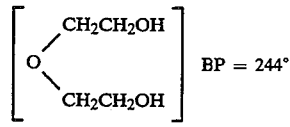

The solution is partially cooled and 20 g of 98% hydrazine hydrate is added. It is then heated at reflux for 15 minutes (to verify that all the ketone has been transformed into hydrazone by TLC).

Cool 30 g of caustic potash in pellet form is added and the mixture is gently boiled for 10 hours.

The mixture is poured onto ice, acidified to a pH of about 7.5 and extracted with ether in countercurrent fashion using heat. The ether solutions are washed with water, dried over anhydrous sodium sulfate, and filtered. The excess solvent is expelled.

The product is distilled under a high vacuum at $BP_{0.2}$ 164° C. and is recrystallized from a mixture of water and alcohol.

Fine light-yellow crystals MP: 77° C.
TLC: Silica gel F-1500 LS-254 Yield: 70%
Solvent: methylene chloride/ethanol: 30/5
$R_f$ about 0.85
—methylene chloride/ethyl acetate: 25/5
$R_f$ about 0.80
The $R_f$ of coumaranone is always smaller than that of coumaran.
$C_9EH_{10}O_3$ Molecular weight: 166.17
The results of elementary analysis are:

|  | calculated | found |
|---|---|---|
| Carbon % | 65.05 | 64.71–64.53 |
| Hydrogen % | 6.06 | 6.02–5.98 |
| Nitrogen % | 28.89 | 28.06–28.41 |

4th step: Preparation of 3,4,4',5'-tetrahydro-5-methoxy-psoralen
Reaction:

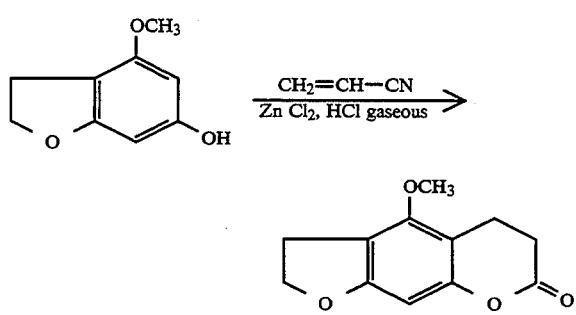

A stream of gaseous HCl is bubbled through a mixture of:
—150 ml of anhydrous ether (dried over sodium)
—4.65 g (or 0.028 mol ) of 6-hydroxy-4-methoxy-coumaran
—3.80 g (or 0.028 mol) of anhydrous zinc chloride
—2.12 g (or 0.01 mol) of acetonitrile (stabilized)
while agitating the solution with a magnetic stirrer and maintaining the solution temperature between 0–5° C.

After 30 minutes, a red oil separates out.

Agitation is continued and gaseous HCl is introduced for an additional two hours.

The reaction mass is kept in the dark for two days.

The ether layer is decanted, 25 ml of water is added to the oil, and the mixture is heated on a boiling water bath for one hour.

The mixture is cooled and extracted several times with ether. The ether solutions are washed with cold water, dried over anhydrous sodium sulfate, filtered, and the excess solvent is expelled.

The crystals obtained can either be sublimated or distilled under high vacuum or recrystallized from petroleum ether ($BP_{40-60°}$ C.).

Yield: 75% fine crystals, MP 175° C.
$C_{12}H_{12}O_4$ Molecular weight: 220.18.
The results of elementary analysis are:

|  | calculated | found |
|---|---|---|
| Carbon % | 65.50 | 65.45–65.70 |
| Hydrogen % | 05.49 | 05.40–05.30 |
| Nitrogen % | 29.07 | 28.80–28.90 |

5th step: Dehydrogenation to obtain 5-methoxy-psoralen
Reaction:

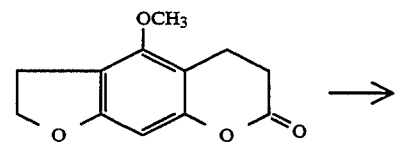

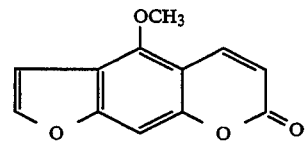

A mixture of
—15 g of diphenyloxide (MP: 28° C.)
—1 g of 3,4,4',5'-tetrahydro-5-methoxy-psoralen
—1 g of 10% palladiumized carbon (fresh), is prepared and heated at reflux for five hours.

The mixture is filtered while hot to remove the catalyst. The excess diphenylether ether is expelled under vacuum or by steam distillation.

The product is recrystallized from ethanol or methanol (1 g soluble in 70 ml of absolute ethanol).

Alternatively, 3,4,4',5'-tetrahydro-5-methoxy psoralen may be dehydrogenated with chloranil or tetrachloro-1,4-benzoquinone or any other dehydrogenating agent, using diphenyloxide or diphenylether-butanol-xylene, etc. as a solvent. The IR UV and NMR spectra are in accordance with those of the literature and identical to those of the natural product. Chromatography under high pressure.

There is no decrease in the eutectic melting point of the mixture of natural product and synthetic product.

Fine colorless pearly flakes MP: 188° C., photosensitive.

Yield: 80%
$C_{12}H_8O_4$ Molecular weight: 216.18
The results of elementary analysis are:

|  | calculated | found |
|---|---|---|
| Carbon % | 66.67 | 66.65–66.85 |
| Hydrogen % | 3.73 | 3.60–3.65 |
| Oxygen % | 29.60 | 29.46–29.48 |

The product obtained from the above process, 5-methoxy psoralen, is useful in the treatment of psoriasis and other skin disorders.

What is claimed is:

1. A method for treating psoriasis in a patient in need of such treatment, comprising administering to said patient orally, a daily dose between 40 to 300 mg of 5-methoxy-psoralen and thereafter exposing said patient to irradiation with A ultraviolet rays having an energy within the range from about 1 to about 10 Joules/cm$^2$.

2. The method of claim 1 comprising administering said 5-methoxy-psoralen orally in solid form.

3. The method of claim 2 comprising administering said 5-methoxy-psoralen in a solid form selected from the group consisting of tablets and capsules.

4. The method of claim 1 wherein said daily oral dose is within the range from about 60 mg to about 150 mg.

5. A method for treating psoriasis in a patient in need of such treatment, comprising topically administering to psoriasis affected areas of said patient, a pharmaceutical formulation containing 100 to 1000 ppm of 5-methoxy-psoralen and thereafter exposing said patient to irradiation with A ultraviolet rays having an energy within the range from about 1 to about 10 Joules/cm$^2$.

6. The method of claim 5 wherein said formulation comprises a solution of said 5-methoxy-psoralen in oil.

7. The method of claim 5 wherein said formulation comprises an aqueous emulsion of said 5-methoxy-psoralen.

8. The method of claim 5 wherein said formulation is an ointment.

* * * * *